United States Patent
Khasnobish et al.

(10) Patent No.: US 10,750,972 B2
(45) Date of Patent: Aug. 25, 2020

(54) SYSTEMS AND METHODS FOR WAVELET BASED HEAD MOVEMENT ARTIFACT REMOVAL FROM ELECTROOCULOGRAPHY (EOG) SIGNALS

(71) Applicant: Tata Consultancy Services Limited, Mumbai (IN)

(72) Inventors: Anwesha Khasnobish, Kolkata (IN); Kingshuk Chakravarty, Kolkata (IN); Debatri Chatterjee, Kolkata (IN); Aniruddha Sinha, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 375 days.

(21) Appl. No.: 15/912,341

(22) Filed: Mar. 5, 2018

(65) Prior Publication Data
US 2018/0338700 A1 Nov. 29, 2018

(30) Foreign Application Priority Data
Mar. 4, 2017 (IN) .............................. 201721007673

(51) Int. Cl.
*A61B 5/0496* (2006.01)
*A61B 5/00* (2006.01)
*A61B 3/113* (2006.01)

(52) U.S. Cl.
CPC ............ *A61B 5/0496* (2013.01); *A61B 3/113* (2013.01); *A61B 5/721* (2013.01); *A61B 5/725* (2013.01); *A61B 5/726* (2013.01); *A61B 5/7207* (2013.01)

(58) Field of Classification Search
CPC ....... A61B 5/0496; A61B 5/725; A61B 5/726; A61B 5/7207; A61B 5/721; A61B 3/113
See application file for complete search history.

(56) References Cited

U.S. PATENT DOCUMENTS

| | | | |
|---|---|---|---|
| 5,360,971 A | | 11/1994 | Kaufman et al. |
| 5,513,649 A | * | 5/1996 | Gevins ................. A61B 5/0476 600/544 |

(Continued)

FOREIGN PATENT DOCUMENTS

CN 102697493 10/2012

OTHER PUBLICATIONS

Barua, S. et al. "A Review on Machine Learning Algorithms in Handling EEG Artifacts," *The Swedish AI Society (SAIS) Workshop*, Stockholm, SE, May 22-23, 2014; 11 pages.

(Continued)

*Primary Examiner* — Mohamed Charioui
(74) *Attorney, Agent, or Firm* — Finnegan, Henderson, Farabow, Garrett & Dunner, LLP

(57) ABSTRACT

This disclosure relates generally to head movement noise removal from electrooculography (EOG) signals, and more particularly to systems and methods for wavelet based head movement artifact removal from electrooculography (EOG) signals. Embodiments of the present disclosure provide for head movement noise removal from the EOG signals by acquiring EOG signals of a user, filtering the acquired EOG signals to obtain a first set of filtered EOG signals, smoothening the first set of filtered EOG signals to obtain smoothened EOG signals, removing one or more redundant patterns and one or more direct current (DC) drifts from the smoothened EOG signals to obtain a second set of filtered EOG signals, and applying, a discrete wavelet transform on the second set of filtered EOG signals to filter a plurality of head movement noise from the second set of filtered EOG signals of the user.

6 Claims, 12 Drawing Sheets

(56) References Cited

U.S. PATENT DOCUMENTS

| | | | |
|---|---|---|---|
| 7,672,717 B1* | 3/2010 | Zikov | A61B 5/0476 600/509 |
| 2010/0240982 A1 | 9/2010 | Westbrook et al. | |
| 2015/0126845 A1* | 5/2015 | Jin | G02B 27/017 600/383 |
| 2015/0230750 A1 | 8/2015 | McDarby et al. | |
| 2017/0140544 A1* | 5/2017 | Farsiu | A61B 5/7203 |

OTHER PUBLICATIONS

Gavali, A. et al. (2016). "Human Eye Mouse," *International Journal of Advance Research and Innovative Ideas in Education*, vol. 2, No. 1; 5 pages.

Bárcia, J. (Mar. 2011). "Human electrooculography interface," *Instituto Superior Técnico, Physics Department*; 11 pages.

Bulling, A. et al. (Mar. 2012). "Multimodal Recognition of Reading Activity in Transit Using Body-Worn Sensors," *Journal ACM Transactions on Applied Perception (TAP)*, vol. 9, No. 1; pp. 2:1-2:21.

Shaviv, B. (1997). "The Design and Improvement of an Eye Controlled Interface," *Department of Computer Science, Stony Brook University, Stony Brook*; 21 pages.

\* cited by examiner

US 10,750,972 B2

SYSTEMS AND METHODS FOR WAVELET BASED HEAD MOVEMENT ARTIFACT REMOVAL FROM ELECTROOCULOGRAPHY (EOG) SIGNALS

PRIORITY CLAIM

This U.S. patent application claims priority under 35 U.S.C. § 119 to: India Application No. 201721007673, filed on Mar. 4, 2017. The entire contents of the aforementioned application are incorporated herein by reference.

TECHNICAL FIELD

This disclosure relates generally to head movement noise removal from electrooculography (EOG) signals, and more particularly to systems and methods for wavelet based head movement artifact removal from electrooculography (EOG) signals.

BACKGROUND

An electrooculogram is the electric potential measured around the eyes, which is generated by the corneo-retinal standing potential between the front and back of the eye. Pairs of electrodes are generally attached either to the left and right of the eyes (horizontal electrooculography component) or above and below the eye (vertical electrooculography component) to measure the eye movements. The horizontal and vertical electrooculography (EOG) components are then obtained by subtracting the signal obtained at one electrode from the signal at the other electrode. Electrooculography (EOG) signals acquire different types of eye movements, which can be employed for human-machine interfaces (HMI) and also for diagnostic purposes. Electrooculography (EOG) signals tend to be contaminated with noise due to unconstrained head movements. This head movement noise or artifact degrades the signal quality as well as increases the misclassification rate of eye movement detection. General filtering and preprocessing techniques are unable to remove this noise. Many traditional systems and methods have previously focused on the signal clarity but none of them have specifically focused on removing the head movement artifacts from the electrooculography signals.

Researchers generally carry out experiments in controlled lab environments, under constrained conditions so as to minimize any sort of contamination of the electrooculography (EOG) signals. Various factors may affect the electrooculography (EOG) signals quality which include power line noise, facial electromyography (EMG), loose electrode contact, and also head movement artifacts. Most of these artifacts can be removed by simple band pass, median, and/or moving average filtering. However the artifacts due to the head movements, in absence of chin rest or constraints of not moving the head, poses to be more problematic as it is in the same frequency range of electrooculography (EOG) signals and also morphologically close to electrooculography (EOG). Researchers have worked on removal of power line, blinks, and facial electromyography (EMG) noise from the electrooculography (EOG). To the best of authors' knowledge none of the existing works have concentrated on presence of head-movement noise in electrooculography (EOG) signals and in turn removal of the same.

The artifacts due to the head movements, in absence of chin rest or constraints of not moving the head, poses to be problematic as it is in the same frequency range of electrooculography (EOG) signals and also morphologically close to electrooculography (EOG). Further, the electrooculography (EOG) signals contaminated with head movement noise tend to misclassification rate of eye movement recognition. Hence, there is a need for a technology that reduces the effect of head movement artifacts and thus to improve the classification accuracy of eye movement detection from electrooculography (EOG) signals.

SUMMARY

Embodiments of the present disclosure present technological improvements as solutions to one or more of the above-mentioned technical problems recognized by the inventors in conventional systems. For example, in one embodiment, a method for filtering a plurality of head movement noise of a user is provided, the method comprising: acquiring one or more electrooculography (EOG) signals of a user; filtering, using a first filter, the one or more acquired electrooculography (EOG) signals to obtain a first set of filtered electrooculography (EOG) signals; smoothening, using a second filter, the first set of filtered electrooculography (EOG) signals to obtain one or more smoothened electrooculography (EOG) signals; removing, one or more redundant patterns and one or more direct current (DC) drifts from the one or more smoothened electrooculography (EOG) signals to obtain a second set of filtered electrooculography (EOG) signals; applying, a discrete wavelet transform, on the second set of filtered electrooculography (EOG) signals to filter a plurality of head movement noise from the second set of filtered electrooculography (EOG) signals of the user; applying, the discrete wavelet transform, on the second set of filtered electrooculography (EOG) signals by: (i) applying, on the second set of filtered electrooculography (EOG) signals, a mother wavelet transform and performing contracting, dilating, and shifting operations of the mother wavelet transform upon the second set of filtered electrooculography (EOG) signals to obtain a set of wavelets; and (ii) decomposing, at one or more decomposition levels, the set of wavelets to filter a plurality of head movement noise from the second set of filtered electrooculography (EOG) signals; and removing one or more redundant patterns and one or more direct current (DC) drifts from the one or more smoothened electrooculography (EOG) signals by applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts.

In another embodiment, there is provided a system for filtering a plurality of head movement noise of a user, the system comprising one or more processors; one or more data storage devices operatively coupled to the one or more processors and configured to store instructions configured for execution by the one or more processors to: acquire one or more electrooculography (EOG) signals of a user; filter using a first filter the one or more acquired electrooculography (EOG) signals to obtain a first set of filtered EOG signals; smoothen using a second filter the first set of filtered electrooculography (EOG) signals to obtain one or more smoothened electrooculography EOG signals; remove one or more redundant patterns and one or more direct current (DC) drifts from the one or more smoothened electrooculography (EOG) signals to obtain a second set of filtered electrooculography (EOG) signals; apply a discrete wavelet transform on the second set of filtered electrooculography (EOG) signals to filter a plurality of head movement noise from the second set of filtered electrooculography (EOG) signals of the user; applying, the discrete wavelet transform, on the second set of filtered electrooculography (EOG) signals by: (i) applying, on the second set of filtered electrooculography (EOG) signals, a mother wavelet transform and perform contracting, dilating, and shifting operations of the mother wavelet transform upon the second set of filtered electrooculography (EOG) signals to obtain a set of wavelets; and (ii) decomposing, at one or more decomposition levels, the set of wavelets to filter plurality of head movement noise from the second set of filtered electrooculography (EOG) signals; and removing the one or more redundant patterns and the one or more direct current (DC) drifts from the one or more smoothened electrooculography (EOG) signals by applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts.

In yet another embodiment, one or more non-transitory machine readable information storage mediums comprising one or more instructions is provided. The one or more instructions when executed by one or more hardware processors causes the one or more hardware processors to perform a method for an optical strobing based multi-frequency vibration measurement, said method comprising: acquiring one or more electrooculography (EOG) signals of a user; filtering, using a first filter, the one or more acquired electrooculography (EOG) signals to obtain a first set of filtered electrooculography (EOG) signals; smoothening, using a second filter, the first set of filtered electrooculography (EOG) signals to obtain one or more smoothened electrooculography (EOG) signals; removing, one or more redundant patterns and one or more direct current (DC) drifts from the one or more smoothened electrooculography (EOG) signals to obtain a second set of filtered electrooculography (EOG) signals; applying, a discrete wavelet transform, on the second set of filtered electrooculography (EOG) signals to filter a plurality of head movement noise from the second set of filtered electrooculography (EOG) signals of the user; applying, the discrete wavelet transform, on the second set of filtered electrooculography (EOG) signals by: (i) applying, on the second set of filtered electrooculography (EOG) signals, a mother wavelet transform and performing contracting, dilating, and shifting operations of the mother wavelet transform upon the second set of filtered electrooculography (EOG) signals to obtain a set of wavelets; and (ii) decomposing, at one or more decomposition levels, the set of wavelets to filter a plurality of head movement noise from the second set of filtered electrooculography (EOG) signals; and removing one or more redundant patterns and one or more direct current (DC) drifts from the one or more smoothened electrooculography (EOG) signals by applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
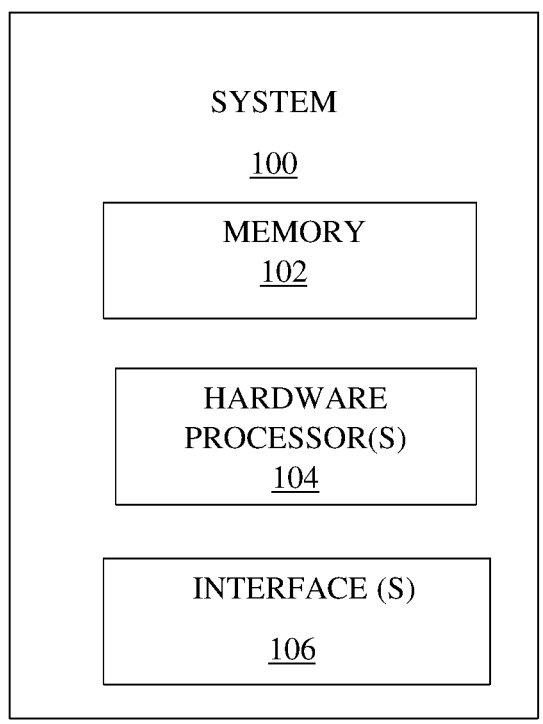
FIG. 1 illustrates a block diagram of a system for wavelet based head movement artifact removal from electrooculography (EOG) signals, according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIGS. 1 through 4E, where similar reference characters denote corresponding features consistently throughout the figures, there are shown preferred embodiments and these embodiments are described in the context of the following exemplary system and/or method.

According to an embodiment of the disclosure, a block diagram of the system 100 is shown in FIG. 1. The system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
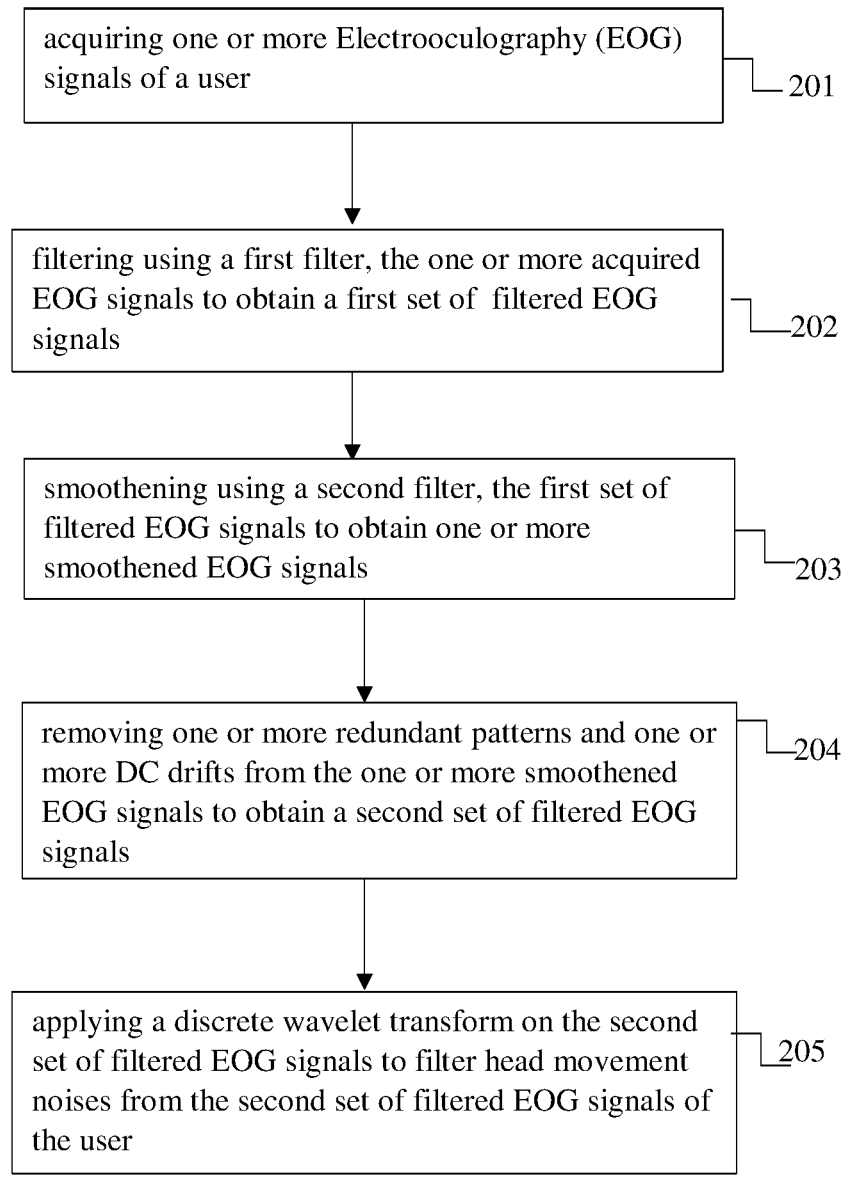
FIG. 2 is a flowchart illustrating the steps involved for wavelet based head movement artifact removal from electrooculography (EOG) signals, according to an embodiment of the present disclosure.

FIG. 2 represents schematic flow illustrating a system and method for wavelet based head movement artifact removal from electrooculography (EOG) signals according to an embodiment of the present disclosure. At step 201, one or more Electrooculography (EOG) signals of a user are acquired. Initially, at step 202, the one or more acquired electrooculography (EOG) signals to obtain a first set of filtered electrooculography (EOG) signals are filtered using a first filter (not shown in FIGS. 1-2). At step 203, the first set of filtered electrooculography (EOG) signals to obtain one or more smoothened electrooculography (EOG) signals are smoothened using a second filter (not shown in FIGS. 1-2). At step 204, removing one or more redundant patterns and one or more DC drifts from the one or more smoothened electrooculography (EOG) signals to obtain a second set of filtered electrooculography (EOG) signals may be performed according to an embodiment of the present disclosure. At step 205, a discrete wavelet transform on the second set of filtered electrooculography (EOG) signals is applied to filter the head movement artifacts from the second set of filtered electrooculography (EOG) signals of the user.

According to an embodiment, the electrooculography (EOG) acquisition system comprises a two channel acquisition system, one each for vertical and horizontal eye movement signals and if further universal serial bus (USB) powered, with a provision of signal isolation achieved by direct current DC/DC converter, which isolates the circuit from USB 5V power and generates a ±12V, which further powers the rest of the circuit. The amplitude and frequency range of electrooculography (EOG) signals are 5-30 µV and 0.01-20 Hz respectively. To avoid signal saturation due to noise, the developed circuit has a total gain of 2400 given in three stages. The circuit further comprises an instrumentation preamplifier with a gain G1=100 where the output of said preamplifier acts an input to passive high pass filter with low cut off frequency of 0.1 Hz, that reduces the direct current (DC) drifts. The high pass filter (HPF) is followed by an active low pass filter of high cut off of 40 Hz and again G2=2.4. The circuit further comprises of an amplifier with a gain G3=10. The electrooculography (EOG) signals are transmitted to PC through 16 bit analogue to digital converter (ADC), National Instruments Universal Serial Bus (NI USB) 6216. The two channel circuit has a current consumption of 9 mA. The sampling rate is 100 Hz. Ag/AgCl electrodes are utilized. The signals are further processed in matrix laboratory (MATLAB) environment, a software platform. The raw electrooculography (EOG) signal for right and left eye movement are depicted in FIG. 3B.

Figure 3A:
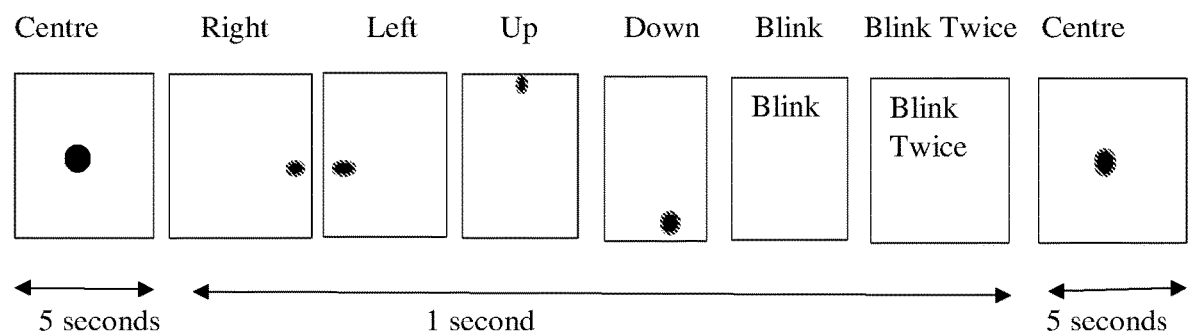
FIG. 3A illustrates visual representation of various eyeball movements during electrooculography (EOG) acquisition, according to an embodiment of the present disclosure.

FIG. 3A illustrates visual representation of various eyeball movements during electrooculography (EOG) acquisition. The electrooculography (EOG) signals acquired comprises of plurality of movements (six movements) types voluntary blinks, single (SB) and double (DB), and up (U), down (D), left (L) and right (R) directions with and without head movement. According to an embodiment of the disclosure, the electrooculography (EOG) system may be utilized to acquire data from few users comprising 4 males and 2 females (27±5 years). The users are first seated at a distance of 120 cm in front of a 17" rectangular computer screen (height: 10 inch, width: 13 inch, approximately), and are presented to visual cues. Referring to FIG. 3A again, the acquisition of electrooculography (EOG) signals with and without head movement noise may be then be performed according to an embodiment, by marking the origin of the user by fixing a cross in the middle of the screen for few seconds; moving the ball of 60 pixel size in the middle of the screen; then the ball either moved up/down/left/right and the user instructed to follow the ball with eyes; and the sequence of ball movement in any direction followed the pattern: center (5 seconds)→left/right/up/down (1 sec)→center (5 seconds). For each direction there were 20 trials per session, and there were total two sessions, thus total 40 trials for each movement type per subject. In addition to this the instruction "BLINK" or "BLINK TWICE" (in font size 97) also appeared on screen, each 20 times in a session, where the subjects needed to blink voluntarily, once or twice, respectively.

Figure 3B:
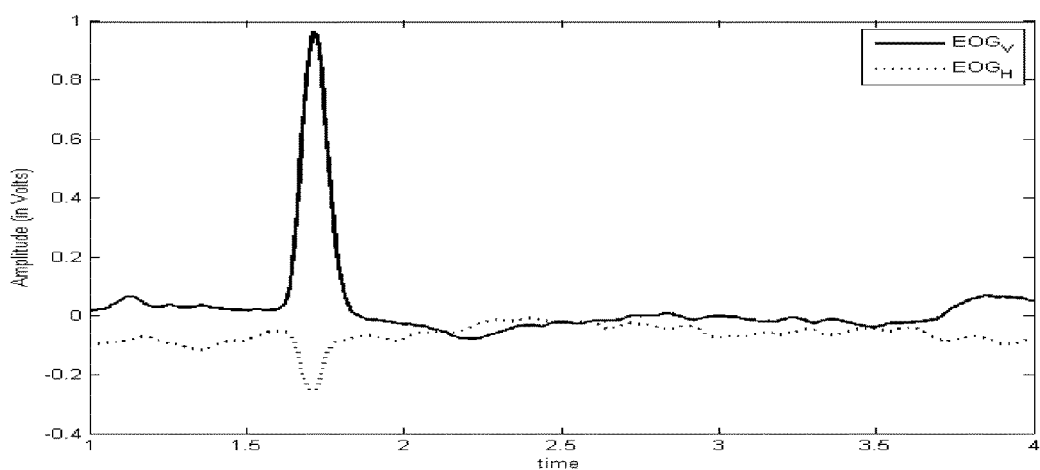
FIGS. 3B through 3M shows the graphical representation of the acquired and preprocessed electrooculography (EOG) signals during six types of eye movements, according to an embodiment of the present disclosure.
Figure 3C:
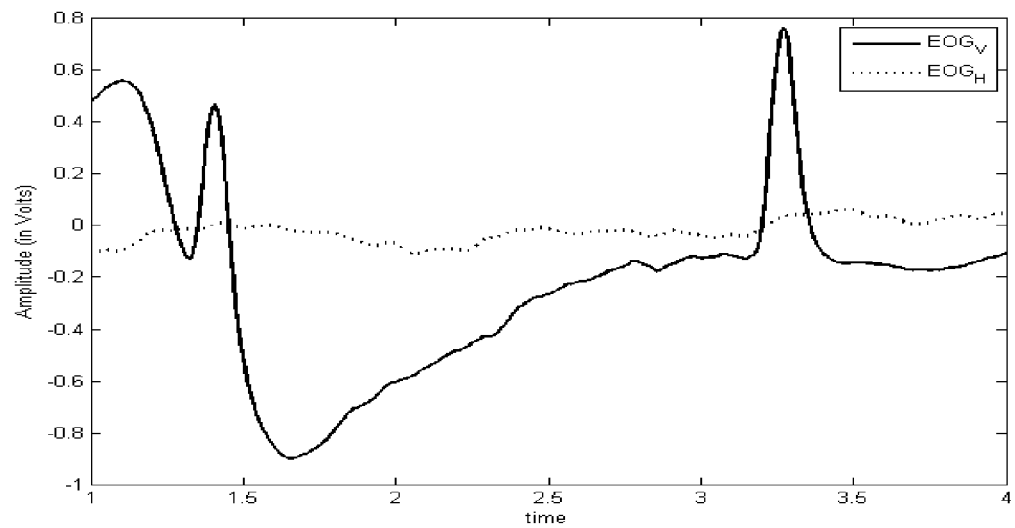
Figure 3D:
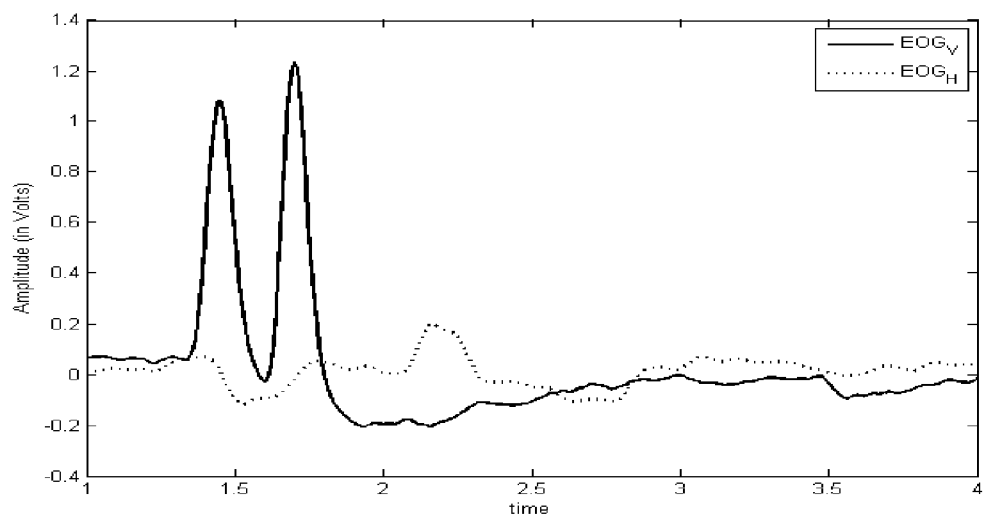
Figure 3E:
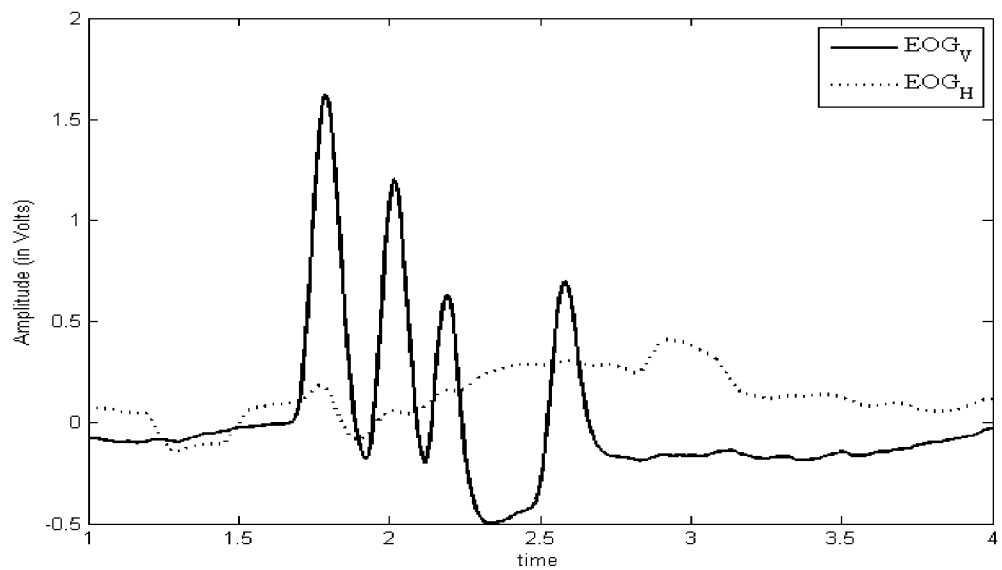
Figure 3F:
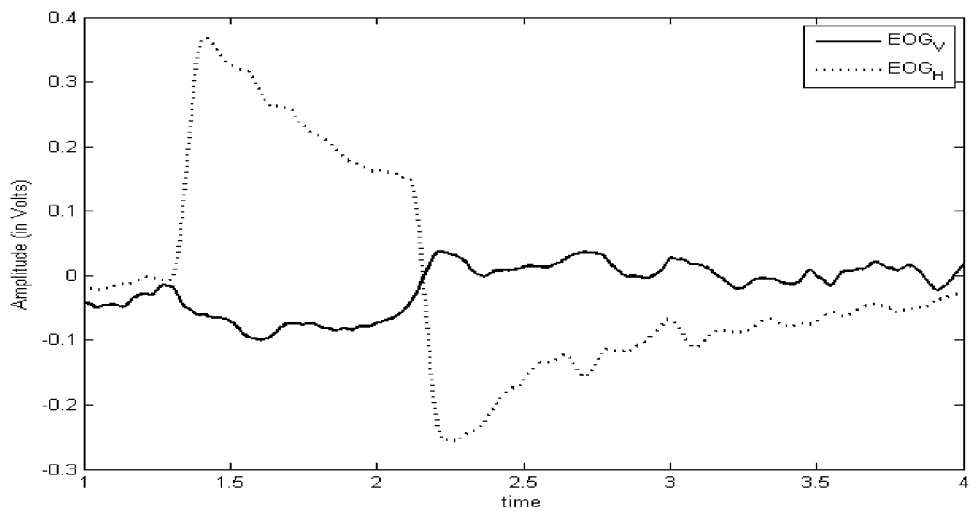
Figure 3G:
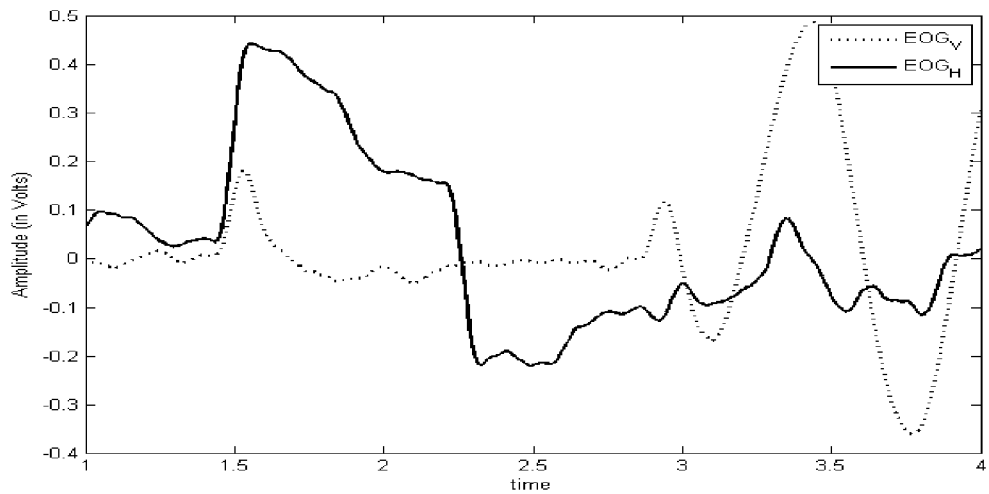
Figure 3H:
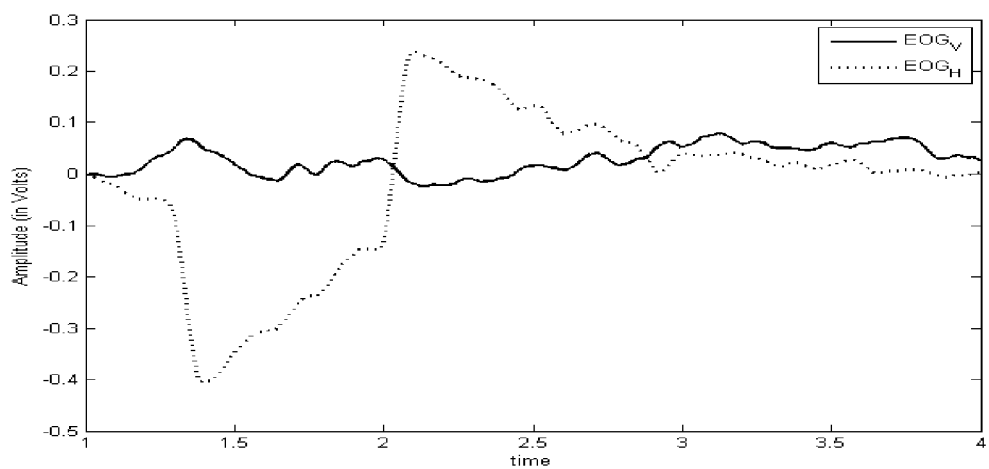
Figure 3I:
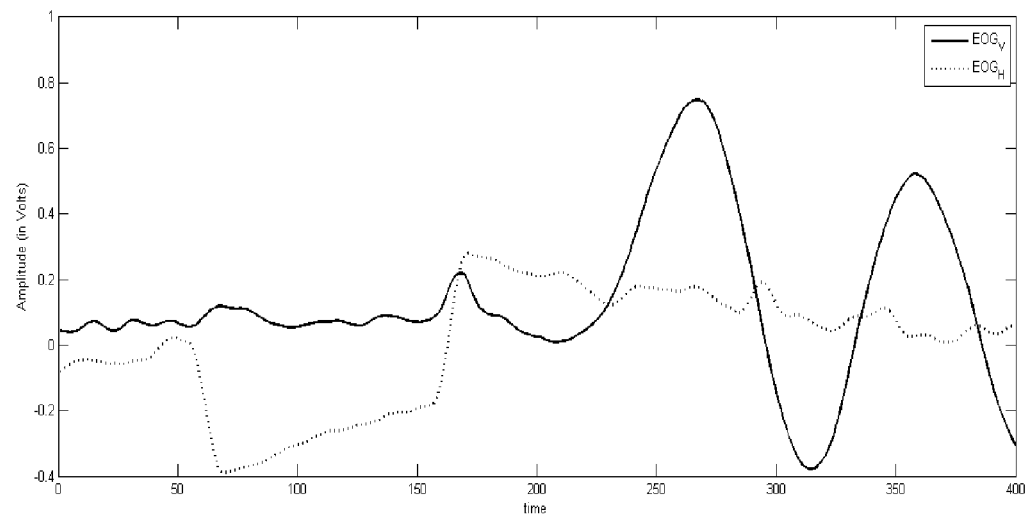
Figure 3J:
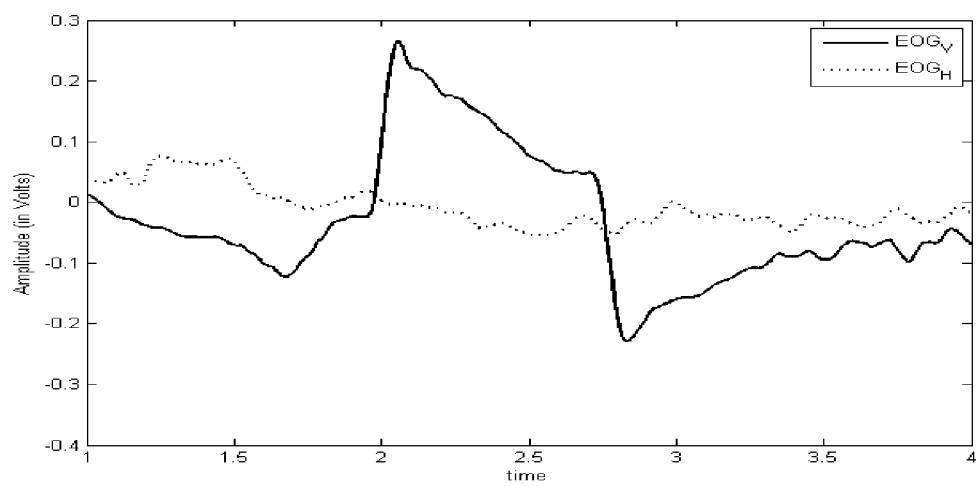
Figure 3K:
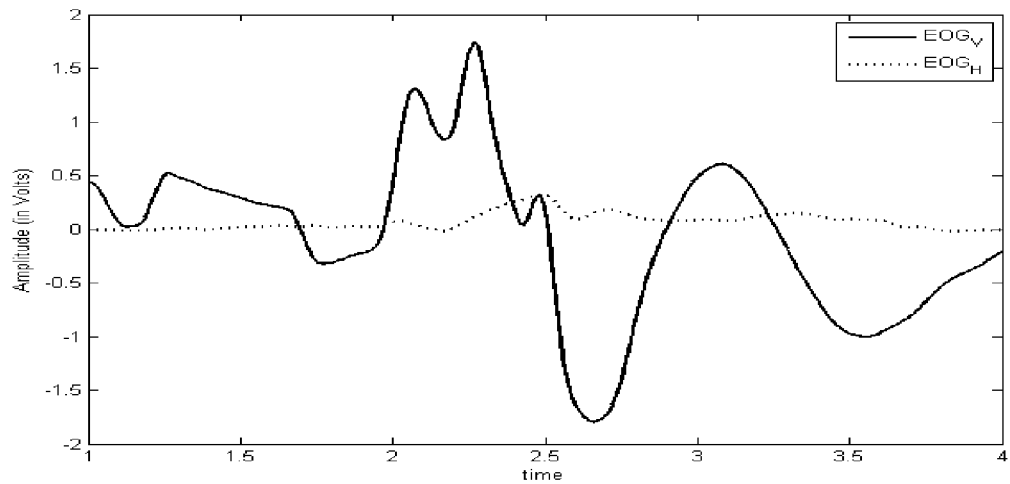
Figure 3L:
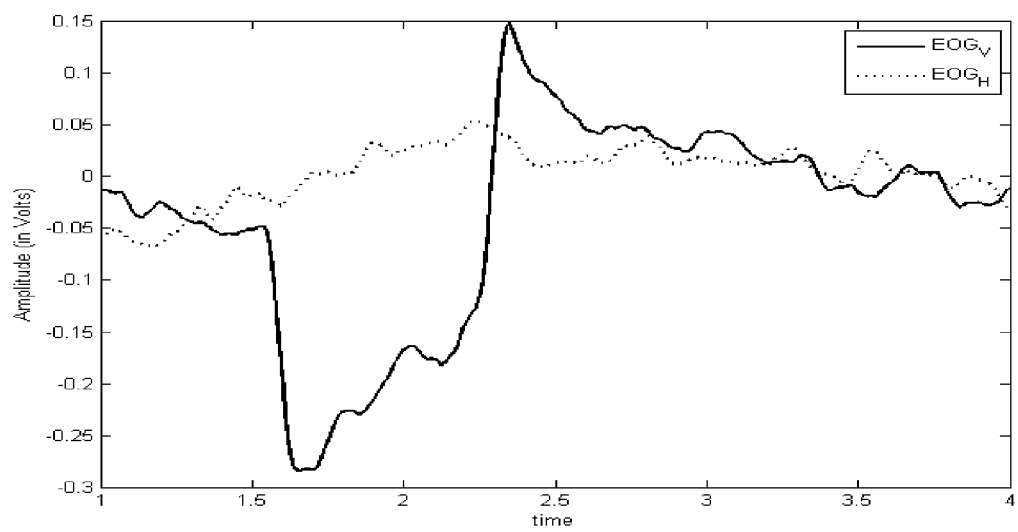
Figure 3M:
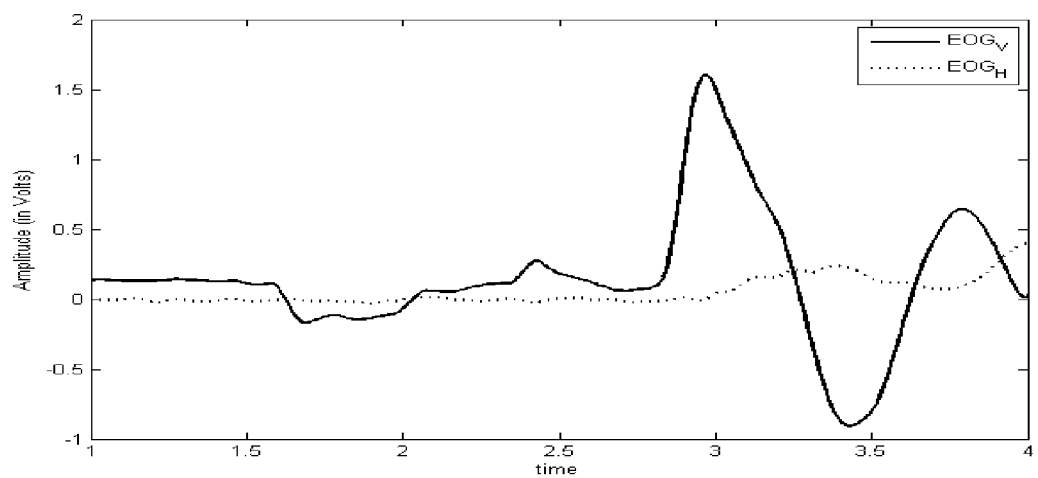

FIGS. 3B through 3M shows the graphical representation of the acquired and preprocessed electrooculography (EOG) signals during six types of eye movements. In FIGS. 3B through 3M, the dotted line denotes $EOG_H$ (horizontal channel EOG) and the solid line denotes $EOG_V$ (vertical channel EOG). FIG. 3B shows single eye blink and may be observed as a positive spike more dominant in the vertical EOG channel. This does not contain head movement noise. FIG. 3C shows single eye blink movement and may be observed as a single positive spike in vertical channel (towards the end of the graph). The deflections at the beginning, in the vertical channel denotes the head movement noise. FIG. 3D shows double eye blinks (consequent two eye blinks) and may be observed as two positive spikes more dominant in the vertical EOG channel. This does not contain head movement noise. FIG. 3E shows double eye blink movement and may observed to be as two positive spikes in vertical channel. The other spikes in the vertical channel denotes the head movement noise. FIG. 3F shows left eye movement and may be observed as a positive pulse like deflection in the horizontal EOG channel, this is devoid of any head movement noise. FIG. 3G shows left eye movement, as a positive pulse like deflection in the horizontal EOG channel. The big deflections in the vertical channel (towards the end of the graph) denotes the head movement noise. FIG. 3H shows right eye movement as a negative pulse deflection seen in the horizontal channel. This does not contain head movement noise. FIG. 3I shows right eye movement as a negative pulse deflection seen in the horizontal channel. The big deflections in the vertical channel (towards the end of the graph) denotes the head movement noise. FIG. 3J shows the up eye movement, as positive pulse like deflection in the vertical EOG channel. It does not contain any head movement noise. FIG. 3K shows the up eye movement, as positive pulse like deflection in the vertical EOG channel (at the beginning of the graph). The other big deflections in the vertical channel denote the head movement noise. FIG. 3L shows the down eye movement, as a negative pulse like deflection in the vertical channel. It does not contain any head movement noise. FIG. 3M shows down eye movement, as a very small negative pulse like deflection in the vertical channel, towards the beginning of the graph. All other big deflections in the vertical channel towards the middle and end shows head movement noise.

Figure 4A:
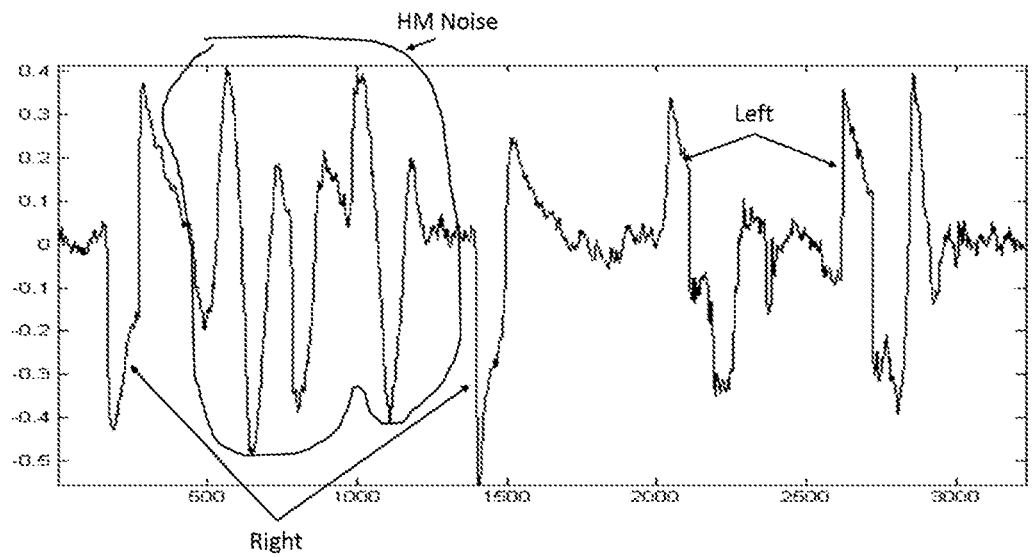
FIGS. 4A through 4E shows the graphical representation of the set of electrooculography (EOG) signals obtained at each stage, according to an embodiment of the present disclosure.
Figure 4B:
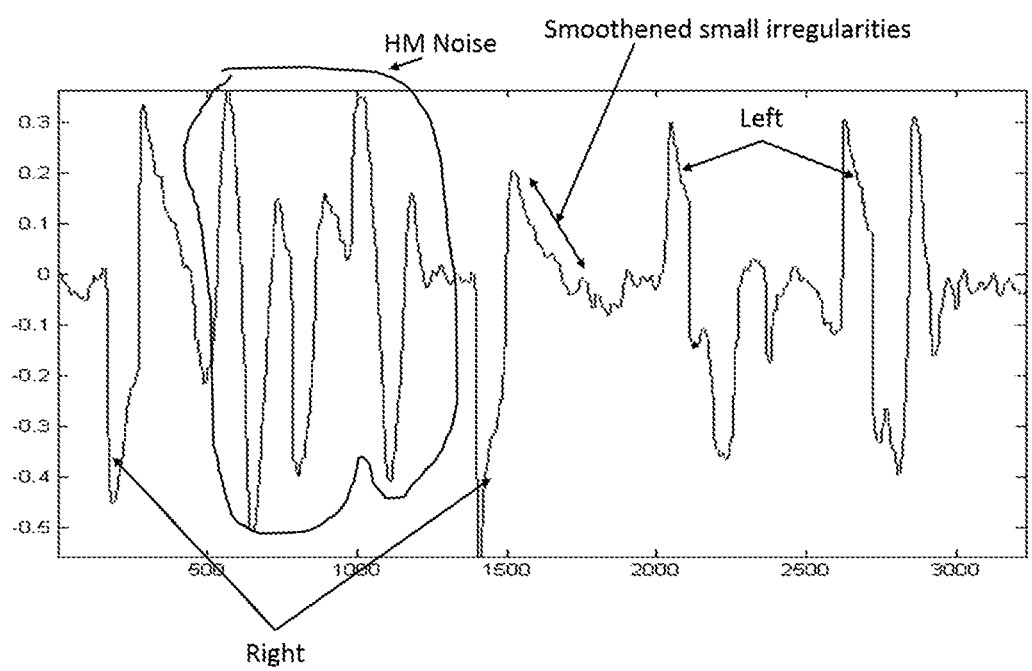
Figure 4C:
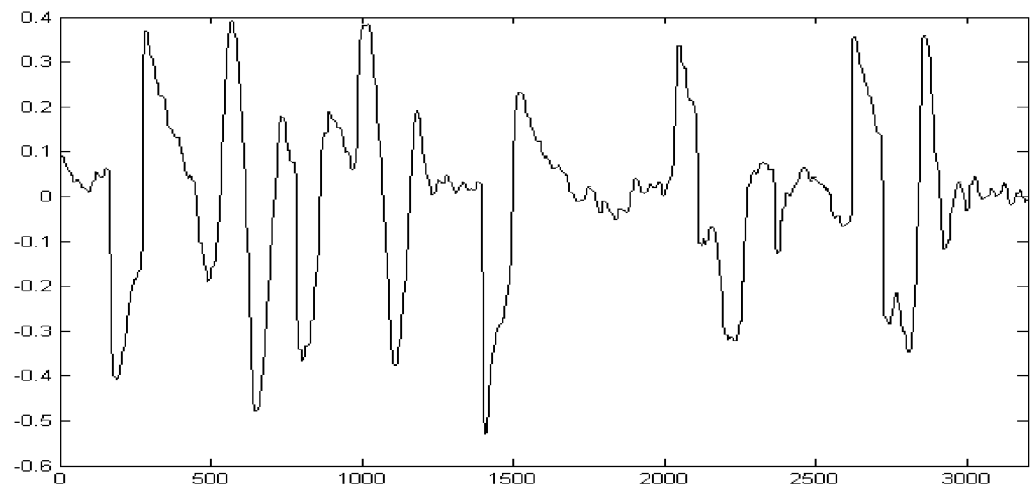
Figure 4D:
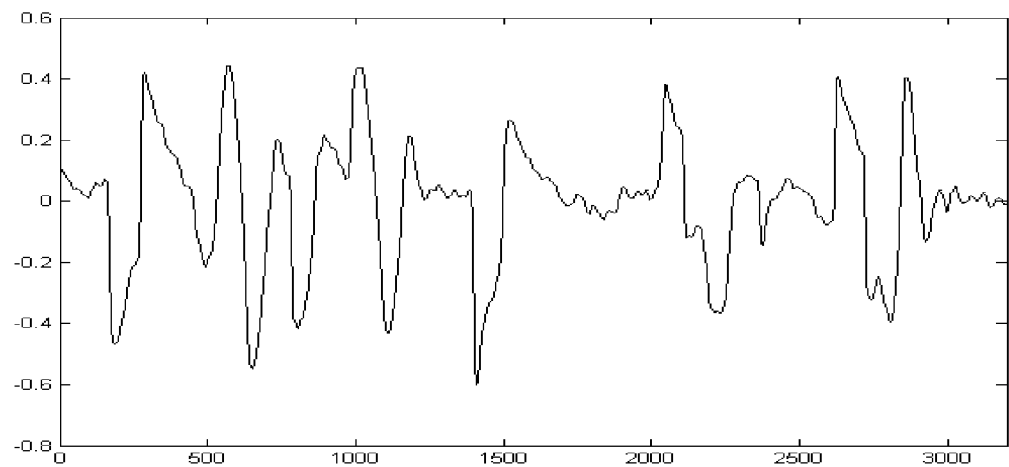
Figure 4E:
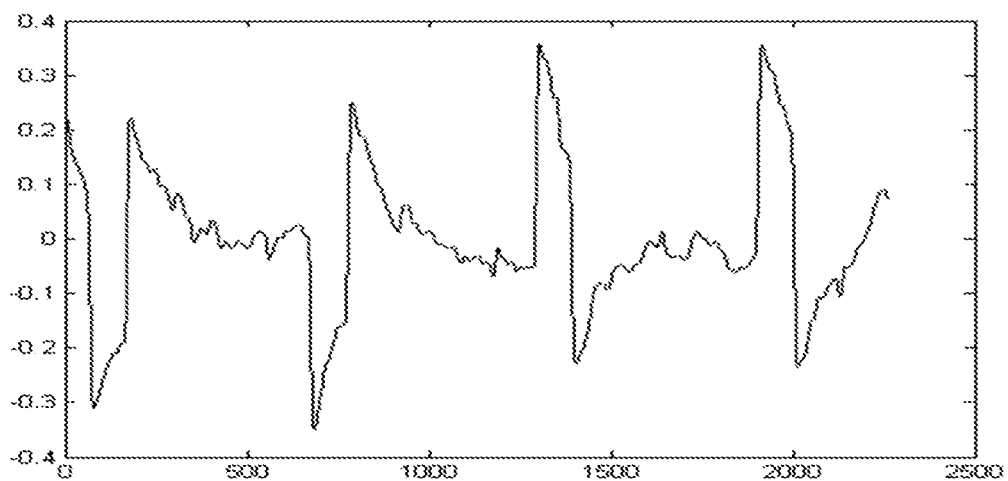

FIGS. 4A through 4E provides graphical representation of the electrooculography (EOG) signals obtained at each stage of the disclosure (from the acquisition till head movement noise removal) may be observed according to an embodiment of the disclosure. Initially, the electrooculography (EOG) signals of a user are acquired using the electrooculography (EOG) acquisition system. These signals are the raw signals acquired with head movement artifacts. Referring to FIG. 4A the acquired electrooculography (EOG) signal of horizontal channel, consisting of left and right eye movements and also head movement noise may be observed. After the acquisition of the electrooculography (EOG) signals, these are filtered using the first filter to obtain first set of electrooculography (EOG) signals which still contain head movement artifacts. The first filter and the second filter are executed by the system 100 and may be stored in the memory 102. According to an embodiment the filtration to obtain first set of electrooculography (EOG) signals may be performed by applying 4th order FIR bandpass filter (referred herein as a first filter) with Hamming window. Referring to FIG. 4B the filtered electrooculography (EOG) signals obtained after applying the first filter (4th order FIR bandpass filter) may be observed. After obtaining first set of filtered electrooculography (EOG) signals, these are further smoothened using a second filter (1-dimensional, 4th order median filter) to obtain smoothened electrooculography (EOG) signals. According to an embodiment this may be performed by applying 1-dimensional, 4th order median filter (referred herein as the second filter), which smoothens the signal. Referring to FIG. 4C, the smoothened electrooculography (EOG) signals may be observed. From the smoothened electrooculography (EOG) signals, redundant patterns and DC drifts are removed to obtain further filtered electrooculography (EOG) signals. According to an embodiment of the present disclosure this may be performed by applying a nth order (eg $6^{th}$ order as discussed below) polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more DC drifts. Referring to FIG. 4D, the electrooculography (EOG) signals after removing redundant patterns and DC drafts may be observed. However these signals still contain head movement artifacts. Finally, the electrooculography (EOG) signals are obtained by applying discrete wavelet transform to the electrooculography (EOG) signals obtained after removing redundant patterns and DC drifts. These electrooculography (EOG) signals do not contain any head movement artifacts. Referring to FIG. 4E), the final electrooculography (EOG) signals without any head movement artifacts may be observed.

According to an embodiment of the disclosure, the removal of a plurality of head movement noise from the acquired electrooculography (EOG) signals may now be considered in detail. The above acquired electrooculography (EOG) signals are filtered, using a first filter to obtain a first set of filtered electrooculography (EOG) signals. In an embodiment, the filtration of the acquired electrooculography (EOG) signals may be performed using $4^{th}$ order FIR bandpass filter with Hamming window according to the equation (1):

$$h(n) = h_d(n)w(n), \text{ and} \quad \text{equation (1)}$$
$$w(n) = 0.54 - 0.46\cos\left(\frac{2\pi n}{M}\right)$$

Where, w(n) is the Hamming window function of finite duration, h(n) is the practical FIR filter, $h_d(n)$ desired IIR filter prototype and M is the filter order. The lower and upper cut-off frequencies are set as 0.5 and 20 Hz respectively.

According to an embodiment of the disclosure, the first set of filtered electrooculography (EOG) signals, also referred to as bandpass filtered signal are further smoothened, by using a second filter to obtain one or more smoothened electrooculography (EOG) signals. In an embodiment this may be performed by applying 1-dimensional, 4th order median filter, which smoothens the signal and at the same time preserves distinctive edges. However, the smoothened electrooculography (EOG) signals still contain some direct current (DC) drifts and redundant patterns as these nonlinear patterns and direct current (DC) drifts are present throughout in the acquired electrooculography (EOG) signals initially and hence they are required to be removed from obtained smoothened electrooculography (EOG) signals to obtain a second set of further filtered electrooculography (EOG) signals to avoid any glitches, inaccuracy in further processing and analysis. The redundant or non-linear patterns and direct current (DC) drifts are removed from said smoothened electrooculography (EOG) signals by applying a $6^{th}$ order polynomial fitting separately to the median filtered vertical (EOG_V) and horizontal (EOG_H) channels of electrooculography (EOG) and by further subtracting the best fitted polynomial from the one or more smoothened electrooculography (EOG) signals to identify and remove the one or more redundant patterns and one or more direct current (DC) drifts. This further provides a second set of further filtered electrooculography (EOG) signals. Referring to FIG. 4E again, the final electrooculography (EOG) signals obtained without head movement artifacts may be observed.

According to an embodiment of the disclosure, the removal of a plurality of head movement noise signals further comprises applying a discrete wavelet transform on the second set of filtered electrooculography (EOG) signals to filter a plurality of head movement noise from the second set of filtered electrooculography (EOG) signals of the user. However, prior to performing discrete wavelet analysis, an eye movement epochs are extracted from the second set of filtered electrooculography (EOG) signals, where each epoch was of 4 seconds window. During real time processing (i.e. online classification), then instead of epoch extraction, signals may be buffered for each 4 seconds. Thus it helps in signal buffering instead of repeated epoch extractions. To avoid demerit of fixed window lengths, the present disclosure applies a discrete wavelet transform as it can discriminate between time and frequency domain characteristics. The step of applying the discrete wavelet transform on the second set of filtered electrooculography (EOG) signals further comprises: applying, on the second set of filtered electrooculography (EOG) signals, a mother wavelet transform (also referred herein as single archetype wavelet transform) and performing contracting, dilating, and shifting operations of a mother wavelet (a single archetype wavelet)

of the mother wavelet transform upon the second set of filtered electrooculography (EOG) signals to obtain a set of wavelets; and decomposing, at one or more decomposition levels, the set of wavelets to filter a plurality of head movement noise from the second set of filtered electrooculography (EOG) signals. The single archetype wavelet, referred to as the mother wavelet is subjected to contraction, dilation, and shifting operations to obtain wavelets. The obtained wavelets are the origin functions that are segregated with respect to time and frequency and are further used to decompose, at one or more decomposition levels, the set of wavelets to filter a plurality of head movement noise from the second set of filtered electrooculography (EOG) signals. This approach forms the basis of wavelet transformation. Mother wavelet may be represented by eq. (2) as:

$$\Psi_{(sc,sh)} = \frac{1}{\sqrt{sc}} \Psi\left(\frac{t-sh}{sc}\right) \quad \text{equation (2)}$$

where sc is the scaling factor and sh is the shifting parameter and sc, sh∈R is the wavelet space.

As the maximum power of the acquired electrooculography (EOG) signals are contained below 15 Hz, the present disclosure perform the decomposition of the set of wavelets to filter head movement noise from the second set of filtered electrooculography (EOG signals) till level 4. The level 4 decomposed wavelets remove the head movement noise and also further retain the signal morphology related to various eye movements. Further, the present disclosure implements biorthogonal 'bior2.8' mother wavelet or single archetype wavelet for decomposing the set of wavelets to filter head movement noise from the second set of filtered electrooculography (EOG) signals as it resembles the eye movements very closely. The biorthogonal wavelet further also provide more degrees of freedom and orthogonal counterparts. The present disclosure applies the discrete wavelet transform for both head movement noise filtering and feature extraction.

The present disclosure also facilitates reduction in signal reconstruction time and computational load as it performs the wavelet transformation based decomposition only and utilizes the obtained decomposed or approximated coefficients for further processing. The present disclosure exploits there types of features, feature set 1 (FS1): the obtained decomposition/approximation coefficients serve as feature set to the classifier, feature set 2 (FS2): sometime-domain parameters and statistical parameters (viz. area under the curve, peak to peak amplitude, maximum and minimum value in a particular epoch window, Hjorth parameters, standard deviation, mean, Skewness, Kurtosis, Shannon's entropy) are extracted from the level 4 approximation coefficients, and iii) feature set 3 (FS3): same time domain and statistical parameters as extracted from preprocessed electrooculography (EOG), prior to wavelet decomposition. These are separately classified. Referring to FIG. 3B electrooculography (EOG_V) denotes the preprocessed and filtered electrooculography EOG.

According to an embodiment of the present disclosure, classification of eye movements from extracted feature sets may be considered. Classification of plurality of eye movements (eg. six eye movements) from the extracted feature sets FS1, FS2 and FS3 are carried out by multiclass k-nearest neighbor (kNN) [21], with k=5 and Euclidean distance as the distance metric Classification results, in the form of confusion matrices (CM), averaged over all subjects for features sets FS1, FS2 and FS3 for 40 trials for each movement type are depicted in Table 1, 2 and 3 respectively. The runtime for classification using feature set FS1, FS2, and FS3 is 0.11 sec, 4.72 sec and 2.55 sec respectively. Referring to tables 1, 2 and 3 below, the system performed best with FS1 followed by FS2 and FS3, moreover FS1 took the least time. Thus the proposed wavelet transform (WT) based denoising as well as feature extraction improves the performance of eye movement recognition system.

Referring to table 1, 2 and 3 below, different types of eye movement are denoted by 'R' (tight eye movement), 'L' (left eye movement), 'U' (up eye movement), 'D' (down eye movement), 'SB' (single blink) and 'DB' (double blink). The table 1 confusion matrices have been obtained while classifying with feature set 1 (FS1). Similarly, table 2 and table 3 confusion matrices have been obtained while classifying with feature set 2 (FS2) and feature set 3 (FS3) respectively. The figures in bold denote the maximum classification accuracy of particular eye movement class among all three feature sets (FS1, FS2 and FS3).

TABLE 1

Confusion matrice (CM) for feature set 1 (FS1)

| CLASSES | | PREDICTED | | | | | |
|---|---|---|---|---|---|---|---|
| | | R | L | U | D | SB | DB |
| TRUE | R | 30 | 0 | 0 | 8 | 2 | 0 |
| | L | 0 | 26 | 1 | 12 | 0 | 1 |
| | U | 2 | 2 | 30 | 5 | 0 | 1 |
| | D | 1 | 0 | 1 | 37 | 0 | 1 |
| | SB | 1 | 0 | 5 | 9 | 25 | 0 |
| | DB | 0 | 0 | 9 | 2 | 10 | 19 |

TABLE 2

Confusion matrice (CM) for feature set 2 (FS2)

| CLASSES | | PREDICTED | | | | | |
|---|---|---|---|---|---|---|---|
| | | R | L | U | D | SB | DB |
| TRUE | R | 28 | 0 | 1 | 8 | 0 | 3 |
| | L | 9 | 13 | 3 | 13 | 1 | 1 |
| | U | 3 | 1 | 22 | 13 | 0 | 1 |
| | D | 0 | 3 | 2 | 34 | 0 | 1 |
| | SB | 5 | 2 | 0 | 1 | 23 | 9 |
| | DB | 3 | 2 | 1 | 0 | 3 | 31 |

TABLE 3

Confusion matrice (CM) for feature set 3 (FS3)

| CLASSES | | PREDICTED | | | | | |
|---|---|---|---|---|---|---|---|
| | | R | L | U | D | SB | DB |
| TRUE | R | 18 | 11 | 1 | 4 | 0 | 6 |
| | L | 8 | 27 | 1 | 1 | 1 | 2 |
| | U | 3 | 0 | 18 | 15 | 1 | 3 |
| | D | 2 | 0 | 3 | 30 | 2 | 3 |
| | SB | 0 | 0 | 0 | 2 | 33 | 5 |
| | DB | 2 | 1 | 0 | 2 | 4 | 31 |

According to an embodiment of the present disclosure, the comparison of the present disclosure with related traditional systems and methods may be considered. The traditional systems and methods fail to consider the head movement noise removal or filtering specifically for acquiring different kinds of eye movements using electrooculography (EOG). Further, the present disclosure has applied discrete wavelet transform for both head movement noise filtering and feature extraction which has significantly improved performance of acquiring different kinds of eye movements using electrooculography (EOG). Referring to table 4 below, Traditional systems and methods 1, Traditional systems and methods 3 and Traditional systems and methods 5 when applied on the present data set, without and with head movement noise have been presented. In Traditional systems and methods 2, Traditional systems and methods 4 and Traditional systems and methods 6, prior to applying Traditional systems and methods 1, Traditional systems and methods 3 and Traditional systems and methods 5 respectively, present disclosure wavelet (WT) based denoising has been implemented, which has improved the classification accuracies (CA) in each of the cases, and the standard deviations (SD) are given in parenthesis have decreased. The bold figures in Table 4 below denote the best classification accuracies. Moreover, unlike other wavelet transform approaches, the present disclosure have utilized the approximation coefficients only. This reduces the time and computational complexity as discussed previously.

TABLE 4

Performance of the present disclosure compared with traditional systems and methods

| Traditional systems and methods | Classification accuracy (CA) in % standard deviations (SD) | |
| --- | --- | --- |
| | Without head movement | Head movement |
| Traditional systems and methods 1 | 86 (2.2) | 81.6 (2.7) |
| Traditional systems and methods 2: WT (present disclosure wavelet) + Traditional systems and methods 1 | 98.3 (0.9) | 93.3 (1.8) |
| Traditional systems and methods 3 | 92.5 (8.6) | 56.2 (4.6) |
| Traditional systems and methods 4: WT (present disclosure wavelet) + Traditional systems and methods 3 | 95 (7.07) | 72.5 (3.3) |
| Traditional systems and methods 5 | 77.6 (4.7) | 72.3 (4.8) |
| Traditional systems and methods 6: WT (present disclosure wavelet) + Traditional systems and methods 5 | 75 (8.3) | 80.5 (4.8) |

The present disclosure considers plurality of eye movements (eg. six types) mentioned above acquired with and without head movement noise. The electrooculography (EOG) signals contaminated with head movement noise tend to misclassification rate of eye movement recognition. The decomposed electrooculography (EOG) signals are extracted by applying discrete wavelet transform to filter head movement artifacts as well as to increase the accuracy of eye movement classification. The present disclosure can be implemented in real time systems as well. The present disclosure when compared with related traditional systems and methods, increase the accuracy of existing works as well as shown in the comparison above.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for filtering a plurality of head movement noise of a user, the method comprising a processor implemented steps of:

acquiring one or more electrooculography (EOG) signals of a user;

filtering, using a first filter, the one or more acquired electrooculography (EOG) signals to obtain a first set of filtered electrooculography (EOG) signals;

smoothening, using a second filter, the first set of filtered electrooculography (EOG) signals to obtain one or more smoothened electrooculography (EOG) signals;

removing, one or more redundant patterns and one or more direct current (DC) drifts from the one or more smoothened electrooculography (EOG) signals to obtain a second set of filtered electrooculography (EOG) signals, wherein removing the one or more redundant patterns and one or more direct current (DC) drifts from the one or more smoothened electrooculography (EOG) signals comprises applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts; and applying, a discrete wavelet transform, on the second set of filtered electrooculography (EOG) signals to filter a plurality of head movement noise from the second set of filtered electrooculography (EOG) signals of the user.

2. The method of claim 1, wherein the step of applying, the discrete wavelet transform, on the second set of filtered electrooculography (EOG) signals comprises:

applying, on the second set of filtered electrooculography (EOG) signals, a mother wavelet transform and performing contracting, dilating, and shifting operations of the mother wavelet transform upon the second set of filtered electrooculography (EOG) signals to obtain a set of wavelets; and decomposing, at one or more decomposition levels, the set of wavelets to filter a plurality of head movement noise from the second set of filtered electrooculography (EOG) signals.

3. A system for filtering a plurality of head movement noise of a user, the system comprising:

a memory storing instructions;

one or more communication interfaces; and one or more hardware processors coupled to the memory via the one or more communication interfaces, wherein the one or more hardware processors are configured by the instructions to:

acquire one or more electrooculography (EOG) signals of a user;

filter using a first filter the one or more acquired electrooculography (EOG) signals to obtain a first set of filtered EOG signals;

smoothen using a second filter the first set of filtered electrooculography (EOG) signals to obtain one or more smoothened electrooculography EOG signals;

remove one or more redundant patterns and one or more direct current (DC) drifts from the one or more smoothened electrooculography (EOG) signals to obtain a second set of filtered electrooculography (EOG) signals, wherein the one or more redundant patterns and the one or more direct current (DC) drifts are removed from the one or more smoothened electrooculography (EOG) signals by applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts; and apply a discrete wavelet transform on the second set of filtered electrooculography (EOG) signals to filter a plurality of head movement noise from the second set of filtered electrooculography (EOG) signals of the user.

4. The system of claim 3, wherein the step of applying, the discrete wavelet transform, on the second set of filtered electrooculography (EOG) signals comprises:

applying, on the second set of filtered electrooculography (EOG) signals, a mother wavelet transform and performing contracting, dilating, and shifting operations of the mother wavelet transform upon the second set of filtered electrooculography (EOG) signals to obtain a set of wavelets; and decomposing, at one or more decomposition levels, the set of wavelets to filter plurality of head movement noise from the second set of filtered electrooculography (EOG) signals.

5. One or more non-transitory machine readable information storage mediums comprising one or more instructions which when executed by one or more hardware processors causes the one or more hardware processor to perform a method for filtering a plurality of head movement noise of a user, said method comprising:

acquiring one or more electrooculography (EOG) signals of a user;

filtering, using a first filter, the one or more acquired electrooculography (EOG) signals to obtain a first set of filtered electrooculography (EOG) signals;

smoothening, using a second filter, the first set of filtered electrooculography (EOG) signals to obtain one or more smoothened electrooculography (EOG) signals;

removing, one or more redundant patterns and one or more direct current (DC) drifts from the one or more smoothened electrooculography (EOG) signals to obtain a second set of filtered electrooculography (EOG) signals, wherein removing the one or more redundant patterns and one or more direct current (DC) drifts from the one or more smoothened electrooculography (EOG) signals comprises applying a nth order polynomial fitting on one or more vertical and horizontal channels of the one or more smoothened electrooculography (EOG) signals to obtain a best fitted polynomial, and subtracting the best fitted polynomial from the one or more smoothened electrooculography (EOG) signals to identify and remove the one or more redundant patterns and one or more direct current (DC) drifts; and applying, a discrete wavelet transform, on the second set of filtered electrooculography (EOG) signals to filter a plurality of head movement noise from the second set of filtered electrooculography (EOG) signals of the user.

6. The one or more non-transitory machine readable information storage mediums of claim 5, wherein the step of applying, the discrete wavelet transform, on the second set of filtered electrooculography (EOG) signals comprises:

applying, on the second set of filtered electrooculography (EOG) signals, a mother wavelet transform and performing contracting, dilating, and shifting operations of the mother wavelet transform upon the second set of filtered electrooculography (EOG) signals to obtain a set of wavelets; and decomposing, at one or more decomposition levels, the set of wavelets to filter a plurality of head movement noise from the second set of filtered electrooculography (EOG) signals.

* * * * *